(12) United States Patent
Truitt et al.

(10) Patent No.: US 6,431,170 B1
(45) Date of Patent: Aug. 13, 2002

(54) FLUID MIXING APPARATUS, METHOD AND SYSTEM USING SAME

(75) Inventors: Patrick W. Truitt, Pittsburgh; Michael Bobeck, Sarver, both of PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/479,136

(22) Filed: Jan. 7, 2000

Related U.S. Application Data
(60) Provisional application No. 60/117,622, filed on Jan. 28, 1999.

(51) Int. Cl.$^7$ ............................................... A61M 15/00
(52) U.S. Cl. ............................ 128/203.12; 128/205.24; 128/207.12; 128/207.16; 137/3
(58) Field of Search ................. 128/205.24, 203.15, 128/203.12, 207.12, 207.16, 203.18, 204.18, 204.23, 203.23; 137/3

(56) References Cited

U.S. PATENT DOCUMENTS

| | | | | |
|---|---|---|---|---|
| 2,674,999 A | * | 4/1954 | Cox ........................ | 128/203.12 |
| 3,913,607 A | * | 10/1975 | Price ........................ | 137/271 |
| 3,977,432 A | * | 8/1976 | Vidal ........................ | 137/604 |
| 4,036,253 A | * | 7/1977 | Fegan et al. ................. | 137/556 |
| 4,543,951 A | * | 10/1985 | Phuc ........................ | 128/204.25 |
| 4,621,634 A | * | 11/1986 | Nowacki et al. ........ | 128/204.18 |
| 4,850,371 A | * | 7/1989 | Broadhurst et al. ......... | 128/719 |
| 5,415,162 A | * | 5/1995 | Casper et al. ........... | 128/203.12 |
| 5,497,765 A | * | 3/1996 | Praud et al. ............ | 128/200.23 |
| 5,522,381 A | * | 6/1996 | Olsson et al. .......... | 128/203.12 |
| 5,558,083 A | * | 9/1996 | Bathe et al. ........... | 128/203.12 |
| 5,752,506 A | * | 5/1998 | Richardson ............ | 128/204.18 |
| 5,793,831 A | * | 8/1998 | Tsiklauri et al. ............. | 379/317 |
| 6,131,571 A | * | 10/2000 | Lampotang et al. ... | 128/204.21 |
| 6,139,506 A | * | 10/2000 | Heinonen ................. | 600/532 |

FOREIGN PATENT DOCUMENTS

DE        3827636 A1 *  2/1989  ............ 128/203.12

* cited by examiner

*Primary Examiner*—John G. Weiss
*Assistant Examiner*—Michael Mendoza
(74) *Attorney, Agent, or Firm*—Michael W. Haas

(57) ABSTRACT

A fluid mixing apparatus and method in a fluid supply system that mixes a secondary fluid flow with a primary fluid flow in such a manner so as to minimize disruption of the fluid flow profile for the primary fluid flow downstream of the mixing point as the secondary fluid flow is introduced to the primary fluid flow. This is accomplished by providing a second conduit carrying the secondary fluid flow that is coupled to a first side of a first conduit carrying the primary fluid flow such that the secondary fluid flow travels around at least a portion of the first conduit. An inlet port arrangement is defined in the first conduit and is arranged such that a size of the inlet port arrangement that introduces the secondary gas flow from the second conduit into the first conduit increases as a distance around the first conduit from the first side increases.

26 Claims, 3 Drawing Sheets

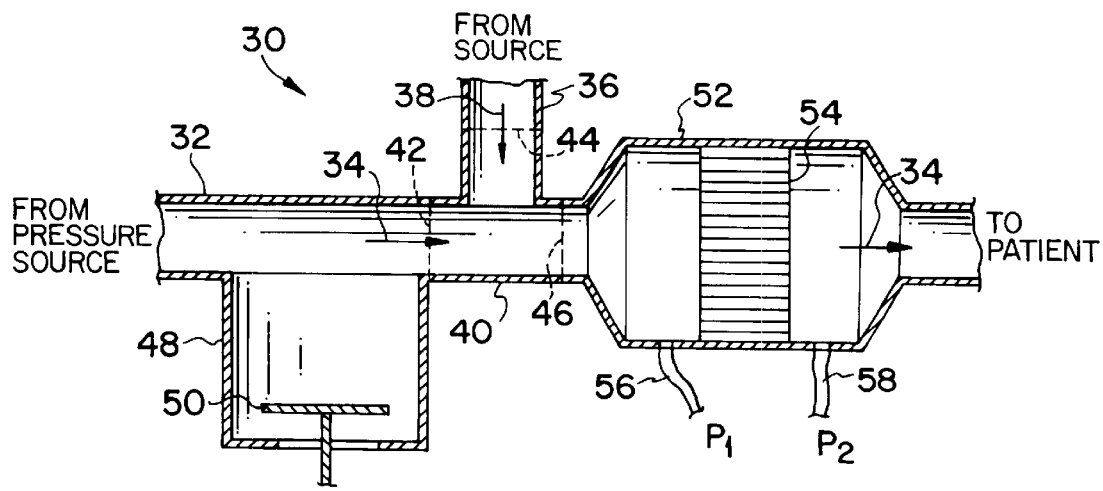
FIG. 1 (PRIOR ART)
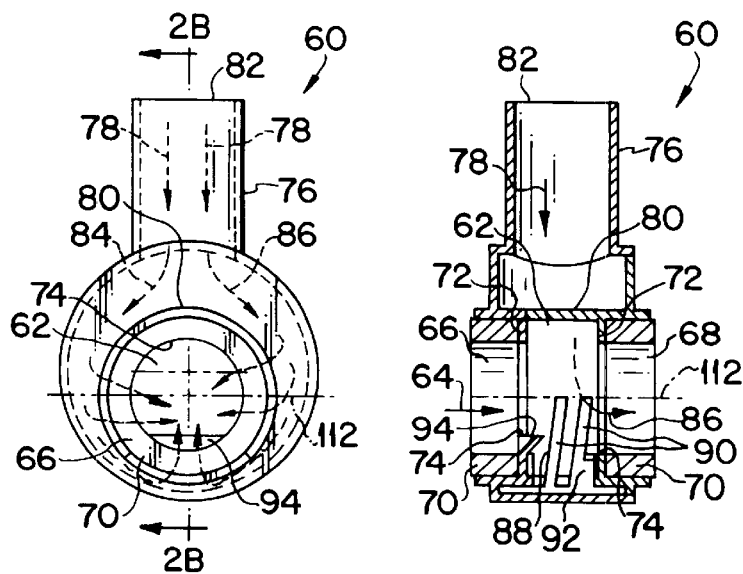
FIG. 2A  FIG. 2B

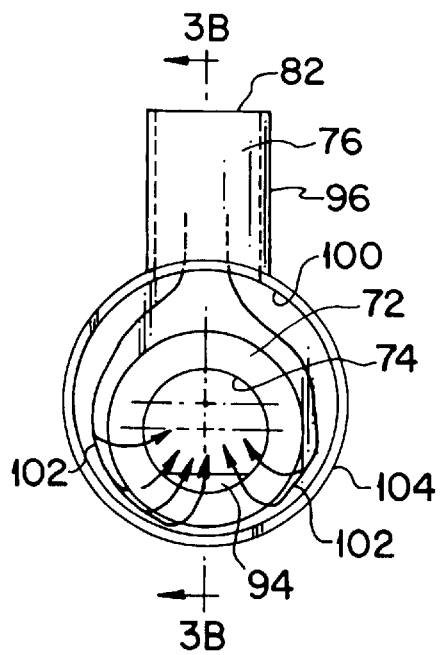
FIG. 3A
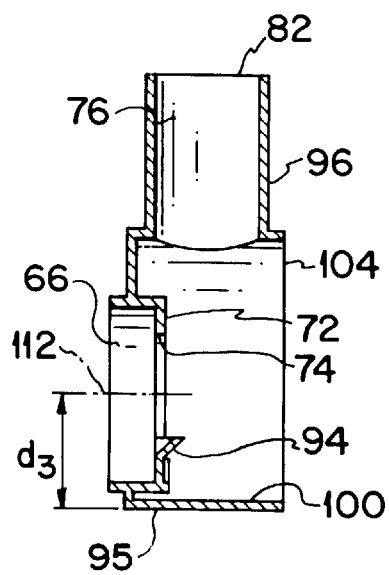
FIG. 3B
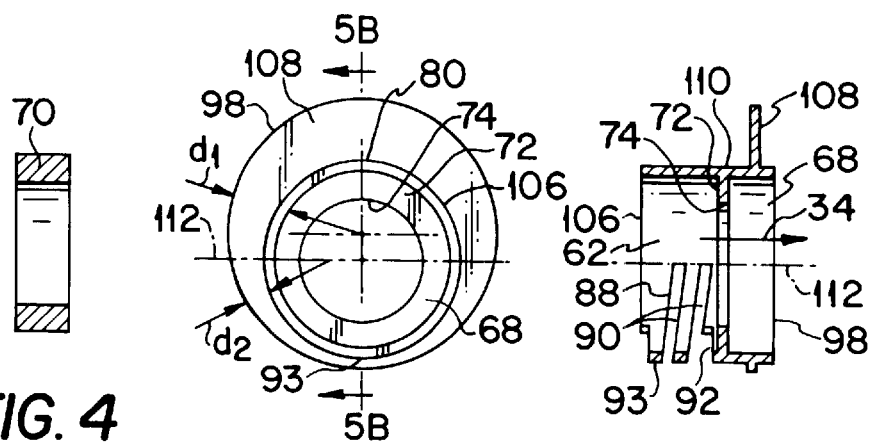
FIG. 4
FIG. 5A
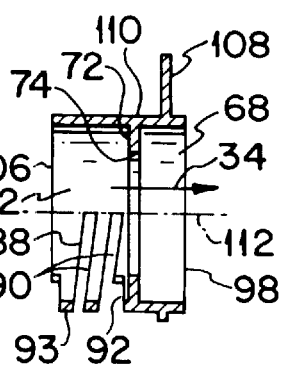
FIG. 5B

FLUID MIXING APPARATUS, METHOD AND SYSTEM USING SAME

CROSS-REFERENCE TO RELATED APPLICATIONS

This application claims priority under 35 U.S.C. §119(e) from U.S. provisional application No. 60/117,622 filed Jan. 28, 1999.

BACKGROUND OF THE INVENTION

1. Field of the Invention

The present invention pertains to an apparatus in a fluid supply system that mixes a primary fluid flow with a secondary fluid flow, and, in particular, to a fluid mixing apparatus, delivery system, and method in which the secondary fluid flow is introduced into the primary fluid flow in such a manner so as to minimize disruption of the fluid flow profile of the primary fluid flow.

2. Description of the Related Art

It is known to provide a flow of breathing gas to a patient to treat a medical disorder. For example, ventilators, either invasive or non-invasive, are used to augment a patient's respiratory effort or to take over that function entirely by providing a flow of breathing gas, such as air, oxygen, or an oxygen mixture, to the patient. It is also known to provide breathing gas to a patient via a pressure support device to treat other breathing disorders, such as sleep apnea syndrome. For example, it is known to use a continuous positive airway pressure (CPAP) device to supply a constant positive pressure to the patient to treat obstructive sleep apnea (OSA). It is also known to provide a positive pressure that varies with the patient's breathing cycle or that varies with the patient's effort to treat OSA and/or ventilate a patient.

Ventilators and pressure support devices typically include a pressure generator, e.g., a blower, piston or bellows, that generates a primary fluid flow at a pressure that is elevated above ambient pressure. A patient circuit delivers this flow of breathing gas from the pressure generator to an airway of the patient. In treating OSA, the pressure delivered to the patient's airway "splints" the airway, thereby preventing its collapse, which is a cause of OSA. A patient interface device, such as a nasal and/or oral mask, trachea tube, or nasal cannula, couples the patient circuit to the patient's airway for delivering the positive pressure breathing gas to the patient.

When using a pressure generating system, such as a ventilator or pressure support device, to deliver a primary flow of breathing gas to a patient, it is often also desirable to provide the patient with a secondary fluid flow, such as oxygen, an oxygen mixture, therapeutic gases or a medicated gas, in addition to the primary fluid flow, which is typically air. It is conventional to introduce the secondary fluid flow into the patient conduit in which the primary fluid flow is traveling. This is often done in the ventilator or pressure support housing itself so that the introduction of the secondary fluid flow can be measured and/or controlled in the pressure generating system. FIG. 1 illustrates a portion of such a conventional fluid delivery system in which a secondary fluid flow is introduced into a primary fluid flow in a pressure generating system As shown in FIG. 1, a conventional fluid delivery system 30 includes a first conduit 32 that carries a primary fluid flow from a source thereof (not shown), such as a pressure generator or a tank of pressurized fluid, to a patient (also not shown). Arrow 34 indicates a main direction of travel for the primary fluid flow in first conduit 32. A second conduit 36 carries a secondary fluid flow from a source thereof (not shown), such as an oxygen concentrator or tank containing the secondary fluid, to first conduit 32. Arrow 38 indicates a main direction of travel for the secondary fluid flow in second conduit 36. In this conventional system, a T-joint 40 couples second conduit 36 to first conduit 32. Due to space limitations in the ventilator/pressure support device, the T-joint is positioned very close to the other components in the fluid delivery system. Dashed lines 42, 44, and 46 illustrate where T-joint 40 couples to the fluid delivery system.

Conventional fluid delivery system 30 also includes a pressure regulation valve 48 upstream of T-joint 40. In pressure regulation valve 48, a valve member 50 moves between an open and closed position to vent fluid from first conduit 32, thereby controlling the pressure of the primary fluid flow in first conduit 32. Valve member 50 is shown in an 40 open position in FIG. 1. A flow meter 52 is coupled to first conduit 32 immediately downstream of T-joint 40. A typical flow meter measures the flow of fluid passing therethrough by measuring a pressure differential on either side of a flow element 54, which induces a pressure drop in the primary fluid flow to create this pressure differential. Typically, relatively small conduits 56 and 58 are provided on each side of flow element 54 for communicating pressures $P_1$ and $P_2$, respectively, on either side of the flow element to pressure sensors (not shown) so that the pressure differential can be determined. Once this pressure differential is known, the flow rate of the primary fluid flow through the flow meter can be determined. The fluid flow exiting flow meter 52 is delivered by first conduit 32 to the patient, and a patient interface device (not shown), as discussed above, couples the first conduit to the patient's airway. It should be noted that other flow meters, pressure sensors, bacteria filters, temperature sensors, humidifiers, valves and other elements can be provided at other locations in the first and second conduit. However, due to space constraints in conventional fluid delivery systems, pressure regulation valve 48 is preferably immediately upstream of T-joint 40 and flow meter 52 is immediately downstream, i.e., adjacent, T-joint 40.

There is a significant drawback to the above-described fluid delivery system. As the secondary fluid flow enters the primary fluid flow at T-joint 40, the secondary fluid flow disrupts the fluid profile of the primary fluid flow. The fluid profile of the primary fluid flow entering flow meter 52 affects the differential pressure across flow element 54. That is, different fluid profiles for the primary fluid flow entering the flow meter can cause the flow meter to register different flow rates and, hence, flow volumes, even though the actual flow and volume of fluid through the system remains unchanged. This is due to the specific calibration of the flow meter for a particular fluid profile and/or the turbulence resulting from directing the secondary fluid flow at a 90° angle into the primary fluid flow.

One solution for the problem caused by the disruption of the fluid profile in the primary fluid flow due to introducing the secondary fluid flow into the primary fluid flow using a conventional T-joint is to locate the flow meter several pipe diameters downstream of the T-joint. This extra distance between the T-joint and the flow meter gives the primary fluid flow time to settle so that a constant flow profile is again achieved before the fluid enters the flow meter. This solution, however, is not practical because of the limited space in conventional fluid delivery systems and the continuing demand that such systems be kept as small as possible. The extra length for the conduit undesirably increases the size of the housing.

A possible second solution for introducing the secondary fluid flow into the primary fluid flow is to change the pathway of the primary fluid flow and the secondary fluid flow so that the two mix in a homogenous fashion. However, this solution requires a relatively large amount of space for the new pathways, and, perhaps, more importantly, introduces a pressure drop in the primary fluid flow. This pressure drop is undesirable because it adversely affects the operating ability of the ventilation and/or pressure support system. For example, such systems measure flow at the patient based on the measured flow rate at a location distal from the patient and based on the known pressure drop through the patient circuit. Introducing an additional pressure drop in the fluid mixing arrangement alters the operating parameters of the ventilation and/or pressure support system. This alteration requires costly and time consuming adaptation of the ventilation and/or pressure support system to account for the additional pressure drop, or else the performance of system may be impaired or destroyed.

SUMMARY OF THE INVENTION

Accordingly, it is an object of the present invention to provide a fluid mixing apparatus for use in a fluid delivery system that avoids the shortcomings of conventional fluid delivery systems in which two fluids are mixed while minimizing the size of such a system. This object is achieved according to one embodiment of the present invention by providing a fluid mixing apparatus that includes a first conduit adapted to carry a primary fluid flow and a second conduit adapted to carry a secondary fluid flow. The second conduit is coupled to the first conduit such that the secondary fluid flow travels from a first side around at least a portion of the first conduit. An inlet port arrangement is defined in the first conduit for communicating the secondary fluid flow from the second conduit to the first conduit. The inlet port arrangement is configured and arranged such that the secondary fluid flow alters direction before entering the inlet port arrangement and such that a size of the inlet port arrangement increases as a distance around the first conduit from the first side increases. This configuration for a fluid mixing apparatus in a fluid delivery system (1) decreases the velocity of the incoming secondary fluid flow and (2) disperses the secondary fluid flow from a single stream into a plurality of smaller streams that enter the first conduit over a relatively large circumferential area of the first conduit, thereby minimizing the disruption of the fluid profile of the primary fluid flow as the secondary fluid flow is introduced into the primary fluid flow. In addition, this configurations minimizes the flow restrictions in the primary fluid flow, and, hence, the pressure drop of the primary fluid flow through the mixing apparatus that may disrupt the operation of the fluid delivery system, especially a flow meter immediately downstream of the fluid mixing apparatus.

It is yet another object of the present invention to provide a fluid delivery system that does not suffer from the disadvantages associated with conventional fluid delivery systems. This object is achieved by providing a fluid delivery system that includes a first source that provides a primary fluid flow, a second source that provides a secondary fluid flow, and a fluid mixing element. The fluid mixing element includes a first conduit coupled to the first source to carry the primary fluid flow and a second conduit coupled to the second source to carry the secondary fluid flow. The second conduit is coupled to the first conduit such that the direction of the secondary fluid flow is altered by traveling from a first side around at least a portion of the first conduit. An inlet port arrangement is provided in the first conduit to communicate the secondary fluid flow to the first conduit. The inlet port arrangement is configured and arranged such in the first conduit that a size of the inlet port arrangement increases as a distance around the first conduit from the side increases.

It is a further object of the present invention to provide a fluid delivery method that includes mixing a primary fluid flow with a secondary fluid flow that does not suffer from the disadvantages associated with conventional fluid deliver techniques. This object is achieved by providing a method that includes providing a primary fluid flow in a first conduit, providing a secondary fluid flow in a second conduit, and communicating the secondary fluid flow from the second conduit with the primary fluid flow in the first conduit so as to minimize disruption of a fluid flow profile of the primary fluid flow in the first conduit as the secondary fluid flow is introduced into the primary fluid flow in the first conduit. Minimizing disruption of the flow profile of the primary fluid flow is accomplished by providing an inlet port arrangement in the first conduit for communicating the secondary fluid flow from the second conduit to the first conduit in which the size of the inlet port arrangement increases as a distance around the first conduit from the first side increases. In addition, the direction of the secondary fluid flow is altered to reduce its velocity prior to entering the inlet port arrangement.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 1 (Prior Art) is a sectional side view illustrating a conventional fluid supply system;

FIG. 2A is a front view and FIG. 2B is a sectional view taken along line 2B—2B in FIG. 2A of a first embodiment of a fluid mixing apparatus according to the principles of the present invention;

FIG. 3A is a rear view and FIG. 3B is a sectional view taken along line 3B—3B in FIG. 3A of a first portion of the fluid mixing apparatus shown in FIGS. 2A and 2B;

FIG. 4 is a cross-sectional view of a gasket used in the fluid mixing apparatus shown in FIGS. 2A–2B;

FIG. 5A is a front view and FIG. 5B is a sectional view taken along line 5B—5B in FIG. 5A of a second portion of the fluid mixing apparatus shown in FIGS. 2A and 2B;

DETAILED DESCRIPTION OF THE PRESENTLY PREFERRED EMBODIMENTS OF THE INVENTION

Figures 6, 7:
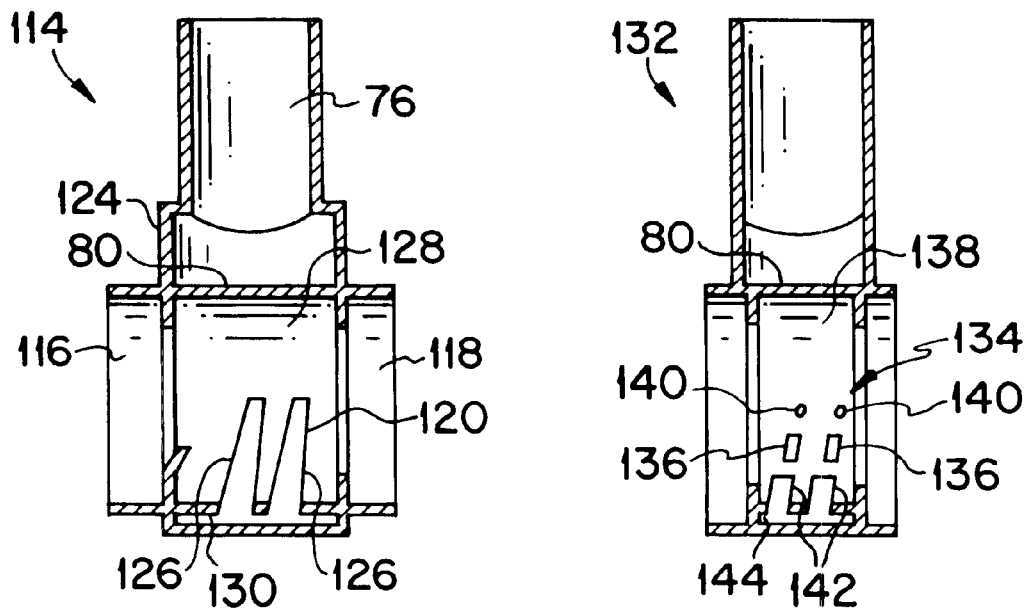
FIG. 6 is a side sectional view of a second embodiment of a fluid mixing apparatus according to the principles of the present invention.
FIG. 7 is a side sectional view of a third embodiment of a fluid mixing apparatus according to the principles of the present invention.

As noted above, FIG. 2A is a front view and FIG. 2B is a sectional view taken along line 2B—2B in FIG. 2A of first exemplary embodiment of a fluid mixing apparatus 60 according to the principles of the present invention. Please note that the "fluid mixing apparatus" is also referred to as a "fluid mixing element." Both terms refer to the same device. In addition, the term "fluid," as used herein, encompasses matter that is gaseous, liquid, or a suspension, for example a liquid or solid suspended in gas or a gas or solid suspended in liquid.

Fluid mixing apparatus 60 inserts into the fluid delivery system, as discussed above with respect to FIG. 1, in place of T-joint 40. Thus, all of the features of a conventional fluid delivery system are applicable to a fluid delivery system that includes fluid mixing apparatus 60, except that fluid mixing apparatus 60 overcomes the disadvantages associated with a T-joint without the drawbacks associated with conventional solutions for correcting the fluid profile disruption problems.

Fluid mixing apparatus 60 includes a first conduit 62 that carries a primary fluid flow in a main direction from a pressure generator to a patient as indicated by arrow 64. A first end 66 of first conduit 62 couples to the fluid delivery system of FIG. 1 at dashed line 42, and a second end 68 couples to the fluid delivery system at dashed line 46 so that the primary fluid flow 64 in FIG. 2B corresponds to primary fluid flow 34 in FIG. 1. In the illustrated embodiment, a gasket 70 is provided at first and second ends 66 and 68 for coupling the fluid mixing apparatus in the fluid delivery system. Walls 72 hold gaskets 70 in place, and orifices 74 defined in walls 72 pass the primary fluid from first end 66 to second end 68. It is to be understood, however, that gaskets 70 can be eliminated or their size and position modified without departing from the principles of the present invention so long as there is substantially no flow restriction in the primary fluid flow that would induce a pressure drop in this flow. If the gaskets are eliminated, walls 72 would likewise be eliminated to ensure that there is no pressure drop across flow mixing apparatus 60 in the primary fluid flow.

A second conduit 76 couples to one side of first conduit 62 for carrying a secondary fluid flow as indicated by arrows 78. The side of first conduit 62 to which the second conduit is coupled is generally indicated at 80. An end 82 of second conduit 76 couples into the fluid delivery system of FIG. 1 at dashed line 44 to receive the secondary fluid from the source thereof. In the illustrated exemplary embodiment, second conduit 76 is configured so as to wrap around each side of first conduit 62 from side 80, where second conduit 76 is coupled to first conduit 62. As a result, the single secondary fluid flow is separated into two streams at location 80. These first and second streams are represented by arrows 84 and 86, respectively, in FIG. 2A. Separating the secondary fluid flow into streams 84 and 86 in this manner effectively reduces the velocity of the flow so that when it is introduced into the first conduit, the disruption caused by the introduction is minimized. In addition, instead of a single relatively large stream that enters the first conduit at one location, the secondary fluid flow is dispersed into a plurality of smaller streams that enter the first conduit over a relatively large circumferential area of the first conduit as discussed below.

Fluid mixing apparatus 60 includes an inlet port arrangement 88 defined in first conduit 62 for communicating the secondary fluid flow, and, in particular, the plurality of relative small streams of the secondary fluid flow, from second conduit 76 to first conduit 62. In an exemplary embodiment of the present invention illustrated in FIGS. 2A–2B and 5A–5B, inlet port arrangement 88 includes a pair of arcuate cutouts 90 defined in the cylindrical shaped first conduit. The uppermost portion of inlet port arrangement 88 begins at a predetermined distance along the circumferential surface of first conduit 62 from location 80, so that the second fluid flow does not flow directly into the first conduit. Instead, the secondary fluid flow must separate and alter directions before entering inlet port arrangement 88. In the illustrated embodiment, the uppermost portion of inlet port arrangement 88 is approximately 90° from the top 80 of first conduit 62. It is to be understood that the location of the uppermost portion of inlet port arrangement 88 can vary so long as a substantial portion of the second fluid flow does not flow directly into the first conduit so as to disrupt the fluid profile of the primary fluid flow therein.

A second cutout 92 is defined in a second side 93 of first conduit 62 opposite first side 80 to maximize a size of the inlet port arrangement at second side 93 of the first conduit. Thus, the largest opening from the second conduit into the first conduit is provided at the side of the first conduit farthest from first side 80, where the second fluid flow is directed at the exterior surface of the first conduit. Maximizing the size of the inlet port arrangement at the distal side of the first conduit relative to the proximal side where the secondary fluid flow is first introduced, is believed to provide a more homogenous mixing of the secondary fluid flow into the primary fluid flow than if the size of the inlet port arrangement remains constant over the circumference of the first conduit.

Arcuate cutouts 90 in first conduit 62 are preferably angled relative to a cross-sectional normal plane of first conduit 62 to facilitate directing the secondary fluid flow in a main direction of travel 64 of the primary fluid flow in first conduit 62. This configuration prevents the secondary fluid flow from entering the first conduit in the same plane normal to a longitudinal axis 112 of the first conduit. Although arcuate cutouts 90 are illustrated such that the uppermost portion is closest to downstream end 68 of first conduit 62, it is to be understood that this angle could be reversed so that the uppermost portion of the arcuate cutout is farthest from downstream end 68 of first conduit 62. In addition, the angle for the arcuate cutout can be varied depending on the amount of room that is provided in the first conduit. Of course, the greater the angle relative to the plane normal to longitudinal axis 112 of the first conduit, the greater the length of conduit that will be needed to accommodate the angle.

As shown in FIGS. 2A and 2B, during normal operation, when a secondary fluid flow, as indicated by arrows 78, is introduced into the primary fluid flow 64, the secondary fluid flow enters inlet 82 of fluid mixing apparatus 60. At location 80 on a first side of first conduit 62, the secondary fluid flow diverges into two streams 84 and 86, each of which travels along either side of the exterior of the first conduit. The uppermost portion of inlet port arrangement 88 is a predetermined distance along the circumferential surface of first conduit 62 from location 80 so that a substantial portion of the secondary fluid flow does not directly enter the first conduit from the second conduit, thereby slowing the velocity of the secondary fluid flow. Each stream of the secondary fluid flow enters the first conduit through inlet port arrangement 88. Because the inlet port arrangement is configured such that the size of the inlet ports increase as the circumferential distance around the first conduit from first side 80 increases, as accomplished, for example, by providing second cutout 92 in side 93 opposite first side 80, the fluid mixing apparatus of the present invention introduces the secondary fluid flow into the primary fluid flow without significantly disrupting the fluid profile. As a result, flow meter 52 immediately downstream of fluid mixing apparatus 60 functions properly.

In a preferred embodiment of the present invention, a lip portion 94 is generally located on side 93 of first conduit 62 opposite side 80 and extends into a passageway defined by the first conduit. Lip portion 94 is sized and arranged so as to prevent a substantial amount of the secondary fluid flow from flowing in a direction opposite that indicated by arrow 64 upon being introduced into the first conduit. Preventing reverse flow is advantageous because, if large enough, the reverse flow can escape through pressure regulation valve 48, resulting in a destroying or degrading of the therapeutic benefit to be provided by the secondary fluid flow. In addition, the reverse flow of gas in the first conduit may adversely affect the operation of the fluid delivery system. If the reverse flow escapes through pressure regulation valve 48, the fluid delivery system may not be capable of accounting for the presence of additional fluid escaping through pressure regulation valve 48. Therefore, the pressure in the first conduit may not be accurately controlled.

It is further preferable for the distal end of lip portion 94 to be angled, for example, at an angle of 45°, to provide a further barrier to reverse flow as well as minimize any pressure drop, i.e., flow restriction, across the fluid mixing apparatus. It is to be understood, however, that angles other than 45° are contemplated by the present invention so long as the functions of preventing backflow and minimizing pressure drop are accomplished.

There are a variety of techniques for manufacturing fluid mixing apparatus 60. An exemplary embodiment of a presently preferred technique is discussed below and is shown in FIGS. 3A–3B and 5A–5B. As shown in these figures, fluid mixing apparatus 60 is essentially a two-piece assembly in which a first piece 96 joins with a second piece 98 to define the fluid mixing apparatus. First piece 96 includes orifice 74, which receives the primary fluid flow from the pressure generator. Wall 72 in which orifice 74 is defined serves as a seat for a gasket so that the first end 66 of the fluid mixing apparatus can be coupled into the fluid delivery system. Of course, gasket 70 held within the ends of the fluid mixing apparatus can be replaced in favor or other techniques for attaching the fluid mixing apparatus into the fluid delivery system. For example, the outer diameter of the ends of the fluid mixing apparatus can match that of the conduit in the fluid delivery system and can be joined to one another in a variety of manners, such as by bonding the ends together or via a gasket into which each conduit is inserted. Alternatively, the diameter of the conduit at the ends of the fluid mixing apparatus can be slightly larger or smaller than the diameter of the conduit to which the end attaches so that a snug fit is maintained, thereby holding the two pieces together.

First piece 96 includes a portion of second conduit 76 that attaches at end 82 to the fluid delivery system. Wall 100 serves as a wall for the portion of second conduit 76 that wraps around the first conduit. The pathway of the secondary fluid flow is generally shown by arrows 102 in FIG. 3A.

Second piece 98 is configured such that it inserts into end 104 of first piece 96. In the assembled configuration, which is shown in FIG. 2B, an end 106 in second piece 98 abuts wall 72 in first piece 96 and a wall 108 seals off second piece 98 off end 104 of first piece 96. Second piece 98 includes a cylindrical portion 110 that corresponds to first conduit 62 so that the primary fluid flow travels in a main direction through the fluid mixing assembly as indicated by arrow 34. As discussed above, inlet port assembly 88 is defined in first conduit 62 to allow the secondary fluid flow to mix with the primary fluid flow.

In the embodiment illustrated in FIGS. 2A–2B, 3A–3B, and 5A–5B, second conduit 76 is configured such that it extends around an entire periphery of the first conduit. In addition, the second conduit is configured such that the cross-sectional area decreases as the second conduit extends from first side 80 around first conduit 62. For example, as shown in FIG. 5A, distance $d_1$ is greater than distance $d_2$, resulting in a decrease in the cross-sectional area of the second conduit from first side 80 to second side 93. It is to be understood, however, that other configurations for the second conduit are contemplated by the present invention. For example, the cross-sectional area of the second conduit need not decrease as the second conduit extends from first side 80 to second side 93 around first conduit 62. On the contrary, the cross-sectional area of the second conduit can remain constant or increase as the second conduit extends from first side 80 to second side 93 around first conduit 62. The illustrated configuration in which the cross-sectional area increases as the second conduit extends from first side 80 to second side 93 around first conduit 62, however, specifically suited to situations where a distance $d_3$ between a centerline 112 of the first conduit and a bottom 95 of the fluid mixing apparatus must be kept to a minimum. See FIG. 3B. If this requirement is lifted, the second conduit need not have a decreasing cross-sectional area.

Figure 8:
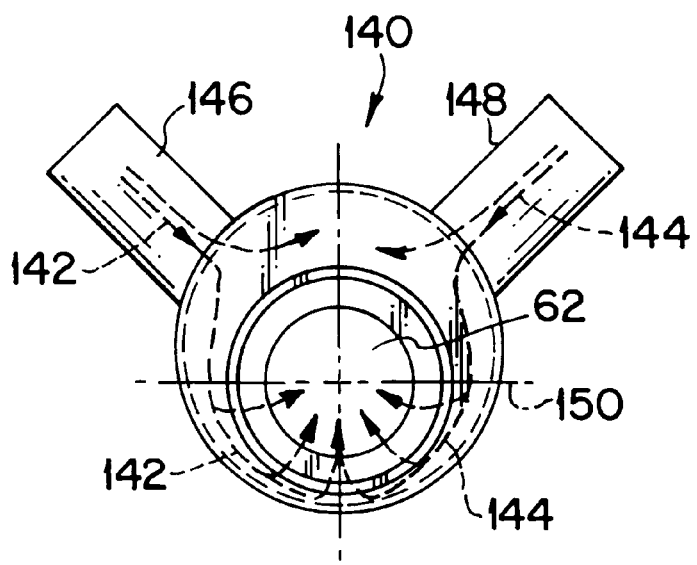
FIG. 8 is a front view of a fourth embodiment of a fluid mixing apparatus according to the principles of the present invention.

Exemplary alternative configurations of the fluid mixing apparatus, according to the principles of the present invention, are discussed below with reference to FIGS. 6–8. Fluid mixing apparatus 114 shown in FIG. 6 is similar to that shown in previous figures except for the configurations of ends 116 and 118 and the configuration of inlet port arrangement 120. Ends 116 and 118 are not recessed into second conduit 122. Instead, they arc flush with wall 124 of second conduit 122. Inlet port arrangement 120, as in the previous embodiment, includes a pair of generally arcuate cutouts 126 in first conduit 128. However, in this embodiment, the width of cutouts 126 increase as a distance from a first side 80, so that the largest area for communicating between the first conduit and the second conduit is provided on a second side 130 of first conduit 128 opposite first side 80. This configuration avoids the need for a second cutout at second side 130 of the first conduit as in the previous embodiment. Preferably, arcuate cutouts 126 are angled relative to a plane normal to the direction of the primary fluid flow, which corresponds to the longitudinal axis of the first conduit, to facilitate homogenous mixing of the secondary fluid flow with the primary fluid flow.

Fluid mixing apparatus 132 shown in FIG. 7 illustrates yet another configuration for inlet port arrangement 134. In this embodiment, the inlet port arrangement is defined by a plurality of holes 136 defined in first conduit 138 to communicate the secondary fluid flow with the primary fluid flow in first conduit 138. Holes 136 can have a variety of configurations. For example, in the illustrated embodiment, the holes 140 closest to first side 80 of first conduit 138 are circular and also have the smallest diameter. The remaining holes are generally rectangular in shape and are sized such that the largest holes 142 are defined in the second side 144 of first conduit 138 opposite first side 80. Preferably, the holes in a direction from first side 80 toward second side 144 are offset to facilitate homogenous mixing of the secondary fluid flow with the primary fluid flow. It is to be understood that the holes can have a variety of configurations and need not be circular or rectangular.

In the previous embodiments, two fluids are mixed in the fluid mixing apparatus. It is to be understood, however, that the present invention contemplates mixing more than two fluid in the fluid mixing apparatus. For example, FIG. 8 illustrates a fluid mixing apparatus 140 in which three fluids are mixed. In particular, a two secondary fluid flows identified by arrows 142 and 144 are introduced into a primary fluid flow carried in first conduit 62. A second conduit 146 carries fluid flow 142 and a third conduit 148 carries fluid flow 144. This mixing apparatus allows, for example, for oxygen as flow 142 and helium as flow 144 to be introduced into a flow of air as the primary fluid flow for delivering hello to the patient. It is to be understood, that more than two secondary fluid flows can be provided and that gases and gas mixtures other than those mentioned above can be provided as the first, second and third fluid flows.

An inlet port arrangement is provided in the first conduit to control the flow of the secondary fluid flows 142 and 144 into first conduit 62. The inlet port arrangement can have any of the configurations as discussed above. For example, the upper most portion of the inlet port arrangement can be located at a centerline 150 of first conduit 62 so that a substantial portion of secondary fluid flows 142 and 144 alter directions before entering the first conduit. Again, the largest opening into the first conduit is preferably provided at a location farthest from second and third conduits 146 and 148.

Each of the illustrated embodiments shows a pair of side-by-side cutouts or sets of holes defined in the first conduit. It is to be understood, however, that only one cutout or one set of holes need be provided. On the other hand, three or more cutouts or sets of holes can be provided in the first conduit depending on the amount of space available in the first conduit.

Furthermore, in each illustrated embodiment, the second conduit extends around the entire periphery of the first conduit. It is to be understood, however, that the present invention contemplates that the second conduit need not extend entirely around the first conduit. On the contrary, the second conduit can extend around only a portion the first conduit like a pair of fingers that do not touch at second side 93, 130, or 144. In this embodiment, the size of the portion of the inlet port arrangement closest to second side 93, 130, or 144, i.e., farthest from first side 80, is larger than portions of the inlet port arrangement closer to first side 80 to ensure homogenous mixing of the secondary fluid flow with the primary fluid flow.

In the illustrated embodiments, the first and second conduits are also illustrated as being generally cylindrical. It is to be understood, however, that other shapes for one or both of these conduits are contemplated by the present invention. For example, the first conduit can have a rectangular cross section.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A fluid mixing apparatus comprising:
   a first conduit adapted to carry a primary fluid flow through said fluid mixing apparatus, wherein said first fluid conduit includes a first end and a second end, and wherein said first fluid conduit defines a linear path from said first end to said second end through said fluid mixing apparatus;
   a second conduit adapted to carry a secondary fluid flow, said second conduit being operatively coupled to said first conduit between said first end and said second end such that at least a portion of said second conduit is disposed around at least a portion of said first conduit so that said secondary fluid flow is directed at a first side of said first conduit and travels along a path from said first side of said first conduit around at least a portion of said first conduit before entering said first conduit; and
   an inlet port arrangement defined in said first conduit for communicating said secondary fluid flow from said second conduit to said first conduit, said inlet port arrangement being configured and arranged such that said secondary fluid flow alters direction before entering said first conduit and such that a size of said inlet port arrangement increases as a circumferential distance around said first conduit from said first side along said path to a second side of said first conduit opposite said first side increases.

2. A fluid mixing apparatus according to claim 1, wherein said first conduit is generally cylindrical and wherein said inlet port arrangement includes at least one arcuate cutout defined in said first conduit.

3. A fluid mixing apparatus according to claim 2, wherein said at least one arcuate cutout has a generally constant width and wherein said inlet port arrangement includes a second cutout defined in a second side of said first conduit opposite said first side to maximize a size of said inlet port arrangement at said second side of said first conduit.

4. A fluid mixing apparatus according to claim 2, wherein said at least one arcuate cutout is angled relative to a cross-sectional normal plane of said first conduit to facilitate directing said secondary fluid flow in a main direction of travel of said primary fluid flow in said first conduit.

5. A fluid mixing apparatus according to claim 2, wherein said at least one arcuate cutout has a width that increases as a circumferential distance from said first side of said first conduit increases.

6. A fluid mixing apparatus according to claim 1, wherein said first conduit is generally cylindrical and wherein said inlet port arrangement includes a plurality of holes defined in said first conduit, wherein a size of said plurality of holes increases as a circumferential distance from said first side of said first conduit increases.

7. A fluid mixing apparatus according to claim 1, wherein said second conduit extends around an entire periphery of said first conduit.

8. A fluid mixing apparatus according to claim 1, wherein a cross-sectional area of said second conduit generally decreases as said second conduit extends from said first side of said first conduit around said first conduit.

9. A fluid mixing apparatus according to claim 1, further comprising a lip portion extending into a passageway defined by said first conduit, said lip portion being sized and arranged so as to minimize a flow of said secondary fluid flow in said first conduit in a direction opposite a main direction of said primary fluid flow in said first conduit.

10. A fluid mixing apparatus according to claim 9, wherein said lip portion is angled toward said main direction of flow of said primary fluid flow in said first conduit.

11. A fluid mixing apparatus comprising:
   first conduit means for carrying a primary fluid flow through said fluid mixing apparatus along a linear path through said fluid mixing apparatus;
   second conduit means for carrying a secondary fluid flow, wherein said second conduit means is operatively coupled to said first conduit means;
   inlet means for introducing said secondary fluid flow from said second conduit means to said first conduit means; and fluid flow maintaining means, associated with said inlet means, for minimizing disruption of a fluid profile of said primary fluid flow as said secondary fluid flow is introduced into said primary fluid flow and for minimizing a restriction of said primary fluid flow in said first conduit.

12. A fluid mixing apparatus according to claim 11, wherein said fluid flow maintaining means includes at least one inlet port defined in said first conduit means for communicating said secondary fluid flow with said first conduit means, wherein a size of said at least one inlet port increases as a distance around said first conduit means from a first side where the secondary fluid flow is first directed at said first conduit to a second side opposite the first side increases.

13. A fluid mixing apparatus according to claim 11, wherein said first conduit means, said second conduit means, and said inlet means are arranged relative to one another such that said secondary fluid flow alters direction before entering said inlet means.

14. A fluid mixing apparatus according to claim 11, wherein said inlet means includes means for directing said secondary fluid flow in a direction that generally coincides with a direction of travel of said primary fluid flow.

15. A fluid mixing apparatus according to claim 11, further comprising means for minimizing a flow of said secondary fluid flow in said first conduit means in a direction opposite a main direction of said primary fluid flow in said first conduit means.

16. A fluid delivery system comprising:
a first source that provides a primary fluid flow;
a second source that provides a secondary fluid flow; and
a fluid mixing element comprising:
a first conduit having a first end operatively coupled to said first source to carry such a primary fluid flow, wherein said first fluid conduit also includes and a second end, and wherein said first fluid conduit defines a linear path from said first end to said second end through said fluid mixing apparatus,
a second conduit having a first end operatively coupled to said second source to carry such a secondary fluid flow, said second conduit having a second end operatively coupled to said first conduit between said first end and said second end such that at least a portion of said second conduit is disposed around at least a portion of said first conduit so that said secondary fluid flow is directed at a first side of said first conduit and travels along a path from said first side of said first conduit around at least a portion of said first conduit before entering said first conduit, and
an inlet port arrangement defined in said first conduit for communicating said secondary fluid flow from said second conduit to said first conduit, said inlet port arrangement being configured and arranged such that said secondary fluid flow alters direction before entering said first conduit and such that a size of said inlet port arrangement increases as a circumferential distance around said first conduit from said first side along said path to a second side of said first conduit opposite said first side increases.

17. A fluid delivery system according to claim 16, wherein said first conduit is generally cylindrical and wherein said inlet port arrangement includes at least one arcuate cutout defined in said first conduit.

18. A fluid delivery system according to claim 17, wherein said at least one arcuate cutout has a generally constant width and wherein said inlet port arrangement includes a second cutout defined in a second side of said first conduit opposite said first side to maximize a size of said inlet port arrangement at said second side of said first conduit.

19. A fluid delivery system according to claim 17, wherein said at least one arcuate cutout has a width that increases as a circumferential distance from said first side of said first conduit increases.

20. A fluid delivery system according to claim 16, wherein said first conduit is generally cylindrical and wherein said inlet port arrangement includes a plurality of holes defined in said first conduit, and wherein a size of said plurality of holes increases as a circumferential distance from said first side of said first conduit to said second side along said path increases.

21. A fluid delivery system according to claim 16, further comprising a lip portion extending into a passageway defined by said first conduit, said lip portion being sized and arranged so as to minimize a flow of said secondary fluid flow in said first conduit in a direction opposite a main direction of said primary fluid flow in said first conduit.

22. A fluid delivery system according to claim 16, wherein said first source is a flow generator that receives a breathing gas and that generates said primary fluid flow at a pressure greater than an ambient pressure, and wherein said second source is a source for one of oxygen and an oxygen mixture.

23. A fluid delivery system according to claim 16, further comprising:
a pressure regulation valve operatively coupled to said first conduit upstream of said fluid mixing element to control a pressure of fluid in said first conduit; and
a flow element operatively coupled to said first conduit downstream of sad fluid mixing element to measure a characteristic of fluid flow in said first conduit.

24. A fluid delivery method that includes mixing a primary fluid flow with a secondary fluid flow comprising:
providing a primary fluid flow in a first conduit along a linear path;
providing a secondary fluid flow in a second conduit;
communicating said secondary fluid flow from said second conduit with said primary fluid flow in said first conduit; and
minimizing disruption of a fluid flow profile of said primary fluid flow in said first conduit as said secondary fluid flow from said second conduit is introduced into said primary fluid flow in said first conduit, wherein minimizing disruption of said fluid flow profiled is accomplished by providing an inlet port arrangement defined in said first conduit for communicating said secondary fluid flow from said second conduit to said first conduit, said inlet port arrangement being configured and arranged in said first conduit such that a size of said inlet port arrangement increases as a distance around said first conduit from said first side, where the secondary fluid flow is first directed at said first conduit, to a second side opposite the first side increases, and such that a direction of said secondary fluid flow is altered before entering said inlet port arrangement.

25. A method according to claim 24, wherein said communicating step includes directing said secondary fluid flow into said primary fluid flow via a cutout defined in said first conduit at an angle relative to a main direction of travel of said primary fluid flow in said first conduit.

26. A method according to claim 24, further comprising minimizing a flow of said secondary fluid flow in said first conduit means in a direction opposite a main direction said primary fluid flow in said first conduit.

* * * * *